(12) United States Patent
Vining

(10) Patent No.: US 10,004,757 B1
(45) Date of Patent: Jun. 26, 2018

(54) ORAL SUPPLEMENT

(71) Applicant: Nutri Vida, LLC, Chatham, NJ (US)

(72) Inventor: Donna Vining, Chatham, NJ (US)

(73) Assignee: Nutri Vida, LLC, Chatham, NJ (US)

( * ) Notice: Subject to any disclaimer, the term of this patent is extended or adjusted under 35 U.S.C. 154(b) by 0 days. days.

(21) Appl. No.: 15/712,984

(22) Filed: Sep. 22, 2017

(51) Int. Cl.
*A61K 31/122* (2006.01)
*A61K 31/685* (2006.01)
*A61K 9/00* (2006.01)
*A61K 31/455* (2006.01)

(52) U.S. Cl.
CPC .......... *A61K 31/685* (2013.01); *A61K 9/0053* (2013.01); *A61K 31/122* (2013.01); *A61K 31/455* (2013.01)

(58) Field of Classification Search
CPC ........................ A61K 31/122; A61K 31/455
See application file for complete search history.

(56) References Cited

U.S. PATENT DOCUMENTS

| | | | |
|---|---|---|---|
| 7,815,943 B2 | 10/2010 | Hennen | |
| 8,349,376 B1 | 1/2013 | Bezzek | |
| 8,747,915 B1 * | 6/2014 | Giampapa | A61K 36/00 424/725 |
| 8,815,310 B2 | 8/2014 | Naghavi et al. | |
| 9,211,277 B2 | 12/2015 | Young et al. | |
| 2005/0053674 A1 | 3/2005 | Niedzwiecki et al. | |
| 2006/0257502 A1 | 11/2006 | Liu | |
| 2008/0305096 A1 * | 12/2008 | Verdegem | A61K 9/148 424/94.4 |
| 2014/0308248 A1 | 10/2014 | Giampapa | |
| 2014/0314729 A1 | 10/2014 | Patel | |
| 2014/0335061 A1 | 11/2014 | Tripp et al. | |
| 2015/0328276 A1 | 11/2015 | Taal et al. | |

FOREIGN PATENT DOCUMENTS

AU 2006202171 12/2006

OTHER PUBLICATIONS

Skoczynska, Unsaturated Fatty Acids Supplementation Reduces Blood Lead Level in Rats, BioMed Research International, Apr. 27, 2015, vol. 2015, Article ID 189190, 9 pages, Hindawi Publishing Corporation.*
Wilson, Soy lecithin reduces plasma lipoprotein cholesterol and early atherogenesis in hypercholesterolemic monkeys and hamsters: beyond linoleate, Atherosclerosis, May 4, 1998, pp. 147-153, Elsevier Science Ireland Ltd.*
Skoczynska, Unsaturated Fatty Acids Supplementation Reduces Blood Lead Level in Rats, BioMed Research International, Apr. 27, 2015, vol. 2015, Article ID 189190, 9 pages, Hindawi Publishing Corporation.
Wilson, Soy lecithin reduces plasma lipoprotein cholesterol and early atherogenesis in hypercholesterolemic monkeys and hamsters: beyond linoleate, Atherosclerosis, May 4, 1998, p. 147-153, Elsevier Science Ireland Ltd.

* cited by examiner

*Primary Examiner* — Rosanne Kosson
(74) *Attorney, Agent, or Firm* — Gearhart Law LLC

(57) ABSTRACT

An oral, nonprescription supplement is described which may contain coenzyme Q10, niacin, and lecithin. The supplement may be sold over-the-counter and is intended to improve cardiovascular health. In use, the supplement is to be taken with a food item and to be further taken twice (two times) per twenty-four hour period.

10 Claims, No Drawings

ORAL SUPPLEMENT

CLAIM OF PRIORITY

This application is a United States non-provisional application and claims no priority to any patent or patent application.

FIELD OF THE EMBODIMENTS

The field of the embodiments of the present invention relate to oral supplements, namely oral supplements designed to improve cardiovascular health.

BACKGROUND OF THE EMBODIMENTS

Cardiovascular disease is the major cause of death not only in western countries but also worldwide. The majority of adverse cardiovascular events develop due to the evolution of atherosclerotic lesions in coronary and cerebral arteries. The atherosclerotic process begins in childhood with the development of fatty streaks, which progress to fibrous plaques that may ultimately cause ischemic damage through thrombotic occlusions. Fatty streaks are focal regions of intimal thickening consisting of foam cells (lipid laden macrophages and monocytes), T lymphocytes, and vascular smooth muscle cells that have proliferated and migrated within the intima. Further accumulation of smooth muscle cells, macrophages, connective tissue, and lipid deposits transforms the fatty streak into a fibrous plaque. Advanced lesions are characterized by reactive fibrous caps, revascularization, and a necrotic core consisting of leukocytes, lipids and debris.

Abnormal growth of arterial smooth muscle cells is one of the most important contributing factors to the genesis of atherosclerosis. In response to pathological stimuli, smooth muscle cells initially migrate from the media layer to the intima layer of the arterial wall, and then proliferate within the intima layer. These events are instrumental to the induction of atherosclerotic deposition. Formation of atherosclerotic lesions in the intima layer occurs in a number of cardiovascular diseases including hypertension, atherosclerosis, myocardial ischemia, myocardial infarction and stroke (cerebrovascular accident). Therefore, prevention and/or retardation of the pathological stimulation of smooth muscle growth has become a critical objective of sustained cardiovascular health. Inflammatory responses, either acute or at chronic low levels, exacerbates and accelerates the elaboration and progression of atherosclerotic lesions.

Cardiovascular disease may be treated or alleviated in a number of ways. Preventative medicine contributes significantly toward reducing the global incidence of cardiovascular disease. These preventative measures often encompass health education, counseling, and monitoring of biological parameters. Many individuals, however, take various prescription oral medications, either as a result of cardiovascular disease or as a preventative measure.

Additionally, most orally administered, biologically active, substances must pass from the digestive system into the bloodstream in order to attain bioavailability and therapeutic efficacy. Upon entering the bloodstream, biologically active substances circulate to cells, organs, and tissues, exerting their biological effects. The concentrations of these substances in blood typically vary over time.

In general, serum levels peak shortly after oral administration, followed by achievement of steady state and a gradual decline in effective concentrations as the substance is metabolized. Biologically active substances maintain greatest efficacy when their blood levels are maintained at constant levels or within desired concentration ranges.

An unmet health need exists for a safe and effective method of alleviating cardiovascular abnormalities, and those associated with chronic or low level inflammatory responses.

In particular, individuals and healthcare professionals alike continue to seek an oral supplement, which promotes lowered levels of "bad" cholesterol or low-density lipoprotein (LDL).

The present invention and its embodiments meets and exceeds these objectives.

REVIEW OF RELATED TECHNOLOGY

U.S. Application 2014/0314729 pertains to compositions of matter useful for the treatment of elevated blood cholesterol. In one embodiment a nutraceutical composition is administered to an individual in need of said composition comprised of the following combinations of ingredients: policosanol, niacin, guggul, garlic, *cynara scolymus*, red yeast-rice, ginger, holy basil, L-carnitine, chromium picolinate, coenzyme Q10, pantothenic acid, grape seed extract, *momordica charantia*, and *garcinia indica*.

U.S. Application 2014/0308248 pertains to a dietary supplement system including a dietary supplement composition for oral administration by an individual in the morning, the composition, including (a) a telomere maintenance complex comprised of: Purslane extract (aerial parts); Turmeric rhizome extract (95% curcuminoids); Quercetin dehydrate, Cayenne pepper fruit; Vanadium (as vanadyl sulfate); Fenugreek seed; *Astragalus* root extract, Omega fatty acid complex including linoleic acid; alpha-linolenic acid; oleic acid borage seed oil gamma-linolenic acid), evening primrose oil fish body oil (eicosapentaenoic acid; docosahexaenoic acid); (b) a calorie restriction mimetics and gene expression complex including Trans-resveratrol (from *Polygonum cuspidatum* root extract); Pterostilbene Fisetin 50% (*Buxus microphylla* Sieb (stem and leaf; Alpha lipoic acid, Coenzyme Q-10, Betaine HCl, Sulfur (from methylsulfonylmethane); L-Carnitine tartrate; L-Carnitine HCl, and (c) a free radical scavenger complex, including Green tea leaf extract catechin and polyphenols); Anthocyanins (from bilberry fruit and grape skin extracts).

SUMMARY OF THE EMBODIMENTS

In general, the present invention and its embodiments comprise an oral supplement that is available for non-prescription (over-the-counter) purchase by a user. The oral supplement contains at least a combination of coenzyme Q10, niacin, and lecithin. Coenzyme Q10 is a fat-soluble, anti-oxidant, endogenously synthesized and required for basic cellular function. It occurs in all respiring eukaryotic cells, primarily in the mitochondria. In addition to be a member of the mitochondrial electron transport chain, it also functions importantly in cellular metabolism and participates in aerobic cellular respiration, which generates energy in the form of adenosine triphosphate (ATP). Coenzyme Q10 is compartmentalized intracellularly at multiple sites of biosynthesis, catabolism, and regulation which form the basis of functional specialization Niacin, also known as nicotinic acid or vitamin B3, is an organic compound and represents one of the 20-to-80 essential human nutrients. Together with nicotinamide it constitutes the group known as the vitamin $B_3$ complex.

The B-vitamins comprise a group of eight, water-soluble vitamins that perform essential, closely inter-related roles in cellular functioning, acting as co-enzymes in a vast array of catabolic and anabolic enzymatic reactions. Their collective effects are particularly relevant to numerous aspects of brain function, including energy production, DNA/RNA synthesis/repair, genomic and non-genomic methylation, and the synthesis of numerous neurochemicals and signaling molecules.

Vitamins are a group of organic compounds which are essential for normal physiological Functioning, but which are not synthesized endogenously by the body, and therefore require sequestration in small quantities from dietary intake. In total, humans require adequate amounts of 13 vitamins: four fat soluble vitamins (A, D, E, K) and nine water soluble vitamins, which comprise vitamin C and the eight B vitamins: thiamine ($B_1$), riboflavin ($B_2$), niacin ($B_3$), pantothenic acid ($B_5$), vitamin $B_6$, folate ($B_9$) and vitamin $B_{12}$.

The B vitamins themselves are not grouped on the basis of any chemical structural similarity, but rather with respect to their water solubility and their inter-related, cellular coenzyme functions. In terms of their origins, the B vitamins are typically synthesized by plants. In the plant they perform the same cellular functions as the roles that they will go on to play in the animals that consume them. The exception to this is vitamin $B_{12}$, which is synthesized by bacteria, and is typically sequestered from animal derived foods.

A vast array of processes and enzymes involved in every aspect of peripheral and brain cell function are dependent on niacin derived nucleotides such as nicotinamide adenine dinucleotide (NAD) and NAD phosphate (NADP). Beyond energy production, these include oxidative reactions, antioxidant protection, DNA metabolism and repair, cellular signaling events (via intracellular calcium), and the conversion of folate to its tetrahydrofolate derivative. Niacin receptors are distributed both peripherally in immune cells and adipose tissue, and throughout the brain. Currently established roles of niacin (vitamin B3) include modulation of inflammatory cascades and anti-atherogenic lipolysis in adipose tissue.

Lecithin is a generic term to designate any group of yellow-brownish fatty substances occurring in animal and plant tissues that contain phosphatidylcholines. Lecithin is also a source of choline, an essential nutrient. Clinical studies have demonstrated benefit in acne, in improving liver function, and in lowering cholesterol. Lecithin, a phosphatidylcholine-containing compound, has been shown to lower cholesterol in hyperlipidemic animals and humans, but not in normolipidemic animals and humans.

Choline is a component of lecithin and is a precursor to acetylcholine, which leads to vasodilation in healthy endothelium and vasoconstriction in unhealthy endothelium. Recent studies suggest that lecithin-rich diet can modify cholesterol homeostasis and hepatic lipoprotein metabolism. Considering the phytotherapeutic impact of lecithin, this work hypothesizes that lecithin administration in hypercholesterolemic individuals may reduce cholesterol concentrations by increasing biliary secretion. One of dietary risk factors for dyslipidemias and atherogenesis is the deficiency in the antioxidant intake, in addition to the low consumption of unsaturated fats and fiber.

More recently, it has been suggested that antioxidant substances are capable of reversing endothelial dysfunction caused by hypercholesterolemia and also reduce the number of coronary events. Considering the high cost of medications prescribed to reduce plasma cholesterol and the prospect of their prolonged and costly use, individuals have relied on alternative treatments for the control of hypercholesterolemia. Recent studies suggest that a lecithin enriched diet can modify the cholesterol homeostasis and lipoprotein metabolism. Lecithin, as a component of the human diet, modifies the cholesterol homeostasis in the liver, increasing the activity of HMG-CoA reductase and cholesterol 7 alpha-hydroxylase, and decreasing the microsomal ACAT activity. One of the most spectacular properties of lecithin resides in its ability to reduce the excess of LDL cholesterol. It also promotes the hepatic synthesis in the liver of great amount of HDL, the beneficial cholesterol. Bile acid secretion with high levels of cholesterol and phospholipid elimination is encouraged by lecithin-rich diets when compared with diets without lecithin.

Low-density lipoprotein ("LDL") particles pose a risk for cardiovascular disease. Within the coronary endothelium, LDL becomes oxidized. A complex set of biochemical reactions regulates the oxidation of LDL particles, chiefly stimulated by presence of necrotic cell debris and free radicals in the endothelium. Increasing concentrations of LDL particles are strongly associated with increasing rates of atherosclerotic accumulation of atherosclerosis within arterial walls over time, eventually resulting in abrupt plaque rupture, sometimes decades later, and triggering thrombi formation within the artery opening. While not cholesterol per se, low density lipoprotein (LDL) is associated with elevated cholesterol levels and thus often termed by the general public as, "bad cholesterol." Accordingly, the oral supplement integrates a combination of nutritional components in specific ratios designed to help reduce cholesterol concentrations and promote cardiovascular health.

In one embodiment of the present invention there is an oral supplement comprising: coenzyme Q10; niacin; and lecithin.

In another embodiment of the present invention there is a method of improving cardiovascular health, the method comprising the steps of: administering an oral composition to an individual, the oral composition comprising: approximately 5 mg to approximately 20 mg of coenzyme Q10, approximately 50 mg to approximately 150 mg of lecithin, and approximately 500 mg to approximately 750 mg of niacin.

In yet another embodiment of the present invention there is a method of improving cardiovascular health, the method comprising the steps of: administering an oral composition to an individual, the oral composition comprising: up to 500 mg of coenzyme Q10, up to 500 mg of soy lecithin, and up to 750 mg of a slow-release niacin; wherein a total amount of the coenzyme Q10, the soy lecithin, and the niacin does not exceed 1500 mg per administration of the oral composition; and wherein the oral composition administered to the individual twice per twenty four hour period.

In general, the present invention succeeds in conferring the following, and others not mentioned, benefits and objectives.

It is an object of the present invention to provide a non-prescription oral supplement that can be supplied over-the-counter.

It is an object of the present invention to provide an oral supplement that is chewable.

It is an object of the present invention to provide an oral supplement that is in a gel cap.

It is an object of the present invention to provide an oral supplement that is taken twice (two times) daily.

It is an object of the present invention to provide an oral supplement that has limited adverse effects.

It is an object of the present invention to provide an oral supplement that promotes cardiovascular health.

It is an object of the present invention to provide an oral supplement that further contains a natural flavoring agent.

It is an object of the present invention to provide an oral supplement that is administered to the individual in conjunction with at least one food item.

It is an object of the present invention to provide an oral supplement that utilizes a "slow release" form of niacin.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the term "cardiovascular disease" is intended to refer to all pathological states leading to a narrowing and/or occlusion of blood vessels throughout the body. In particular, the term "cardiovascular disease" refers to conditions including atherosclerosis, thrombosis, and other related pathological states, especially within arteries of the heart and brain. Accordingly, the term "cardiovascular disease" encompasses, without limitation, various types of heart disease, as well as Alzheimer's disease, and vascular dementias.

As used herein, the term "approximately" is intended to refer to the measurable amount. In the present application, the measurable amount is defined in milligrams (mg). The term "approximately" is intended to include the specified amount and variations of the amount of up to ±15%.

When introducing elements of the preferred embodiments(s) of the present invention. The articles "a", "an", "the" and "said" are intended to mean that there are one or more of the elements. The terms "comprising," "constituting," "including," and "having" are intended to be inclusive and mean that there may be additional elements other than the listed elements.

The oral supplement or composition, as described herein, is preferably taken orally (by mouth). However, in other formats the supplement may be taken via other acceptable, delivery channels, such as but not limited to, transcutaneous, transmucosal, intravenous, or the like or some combination thereof. The form factor of the composition may also vary and may include, but not be limited to, a beverage powder (powder to be mixed with liquid), a capsule, a tablet, a solution, or a powder, or the like or some combination thereof.

Generally, the oral supplement is to be administered twice (two times) daily but each may be taken up to three times per day depending on the precise formulation of the supplement. This regimen is preferably continued as needed and may be required to be administered for 8 to 12 weeks before noticeable results are experienced by the user.

The composition preferably contains an amount of coenzyme Q10, niacin, and lecithin. The composition may further contain a natural flavoring agent suitable for the embodiments of the invention may be derived from natural sources such as plants, herbs, spices, animals, microbial fermentations, esters, aldehydes, ketones, and the like or some combination thereof. Various flavorings may include but are not limited to grapefruit, cherry, pineapple, orange, apple, peppermint, herbal, vanilla, tea, chocolate, raspberry, strawberry, cranberry, blueberry, papaya, lemon, lime, champagne, grape, banana, watermelon, honey, peach, orange, pomegranate, plum, coconut, and the like or any combination thereof.

Further, coloring agents (e.g. caramel, red, yellow, black or blends, ferric oxide), binding agents (e.g. lactose powder, sucrose powder, tapioca starch, and microcrystalline cellulose), anti-caking agents (e.g. calcium silicate, magnesium silicate, colloidal silicon dioxide, talc), etc., may be used in conjunction with the other components of the supplement.

The coenzyme Q10 may be present in the composition in an amount of up to 500 mg. In a more preferred embodiment, the coenzyme Q10 is present in an amount of up to 100 mg. In a more preferred embodiment, the coenzyme Q10 is present in an amount of approximately 5 mg to approximately 20 mg.

The lecithin may be present in the composition in an amount of up to 500 mg. In a more preferred embodiment, the lecithin is present in an amount of approximately 50 mg to approximately 150 mg. The lecithin utilized in the composition is preferably a soy-based lecithin may be derived from cottonseed, marine sources, milk, rapeseed, soybeans, and sunflower or some combination thereof. In studies, soy lecithin has been reported to reduce cholesterol levels up to 40% after two months and reduce LDL by upwards of 50% within a similar time frame.

The niacin (vitamin $B_3$) may be present in the composition in an amount of up to 3000 mg. In a more preferred embodiment, the niacin may be present in an amount of up to 750 mg. In a more preferred embodiment, the niacin may be present in an amount of approximately 500 mg to approximately 750 mg. Niacin, when taken over the daily recommended amount may result in increases high-density lipoprotein (HDL) by 20% to 35%, decreases in small low-density lipoprotein (small LDL) particles, decreases in triglycerides by 30%, decreases in very low-density lipoprotein (VLDL) particles, decreases in lipoprotein(a), or Lp(a), decreases in low-density lipoprotein (LDL), usually by 20 mg/dL to 40 mg/dL, or 5% to 25%. Preferably, the niacin contained with the supplement is a slow-release form of niacin.

In one embodiment of the present invention, the oral composition contains approximately 5 mg to approximately 20 mg of coenzyme Q10, approximately 50 mg to approximately 150 mg of lecithin, and approximately 500 mg to approximately 750 mg of niacin. In another embodiment of the present invention, the oral composition contains up to 500 mg of coenzyme Q10, up to 500 mg of soy lecithin, and up to 750 mg of a slow-release niacin. In such a composition, a total amount of the coenzyme Q10, the soy lecithin, and the niacin does not exceed 1500 mg per single administration of the oral composition. In another embodiment of the present invention the oral composition contains up to 100 mg of coenzyme Q10, up to 500 mg of lecithin, and up to 3000 mg of niacin.

The oral composition(s) or supplement of the present application is intended to promote cardiovascular health. The oral composition may be administered up to three times per twenty four hour period, but is preferably administered twice (two times) per twenty-four hour period. In one embodiment, a total amount of the coenzyme Q10, the soy lecithin, and the niacin is not to exceed 1500 mg per single administration of the oral composition. The oral composition in intended to be administered with at least one food item such that the composition is not taken on an empty stomach. This serves to increase the bioavailability of the composition and limit unwanted adverse effects.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method of improving cardiovascular health, the method comprising the steps of:
    administering an oral composition to an individual, the oral composition comprising:
        approximately 5 mg to approximately 20 mg of coenzyme Q10,
        approximately 50 mg to approximately 150 mg of lecithin, and
        approximately 500 mg to approximately 750 mg of niacin.

2. The method of claim 1 wherein the oral composition is in a chewable form.

3. The method of claim 1 wherein the oral composition is in a soft-gel or gel cap.

4. The method of claim 1 wherein the oral composition is administered to the individual up to two times per twenty-four hour period.

5. A method of improving cardiovascular health, the method comprising the step of:
    administering an oral composition to an individual, the oral composition comprising:
        5 mg to up to 500 mg of coenzyme Q10, 50 mg to up to 500 mg of soy lecithin, and 500 mg to up to 750 mg of a slow-release niacin; wherein a total amount of the coenzyme Q10, the soy lecithin, and the niacin does not exceed 1500 mg per administration of the oral composition; and wherein the oral composition is administered to the individual twice per twenty-four hour period.

6. The method of claim 5 wherein the oral composition is administered to the individual in conjunction with at least one food item.

7. The method of claim 5 wherein the oral composition is in a chewable form.

8. The method of claim 5 wherein the oral composition is in a soft-gel or gel cap.

9. The method of claim 5 wherein the oral composition further comprises at least one of a flavoring agent, a binding agent, an anti-caking agent.

10. The method of claim 5 wherein the oral composition is an over the counter supplement.

* * * * *